(12) United States Patent
Fillmore et al.

(10) Patent No.: US 6,277,571 B1
(45) Date of Patent: Aug. 21, 2001

(54) SEQUENTIAL CONSENSUS REGION-DIRECTED AMPLIFICATION OF KNOWN AND NOVEL MEMBERS OF GENE FAMILIES

(75) Inventors: Helen Fillmore, Richmond; William Broaddus, Midlothian; George Gillies, Earlysville, all of VA (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 0 days.

(21) Appl. No.: 09/163,485

(22) Filed: Sep. 30, 1998

Related U.S. Application Data

(60) Provisional application No. 60/108,152, filed on Oct. 3, 1997.

(51) Int. Cl.[7] .............................. C12Q 1/68; C12P 19/34; C07H 21/02; C07H 21/04
(52) U.S. Cl. ........................ 435/6; 435/91.2; 536/23.1; 536/24.3
(58) Field of Search .................. 435/6, 91.2; 536/23.1, 536/24.3; 935/76, 77, 78

(56) References Cited

U.S. PATENT DOCUMENTS

| | | |
|---|---|---|
| 5,262,311 | 11/1993 | Pardee et al. . |
| 5,437,975 | 8/1995 | McClelland et al. . |
| 5,527,669 * | 6/1996 | Resnick et al. . |
| 5,599,672 | 2/1997 | Liang et al. . |

FOREIGN PATENT DOCUMENTS

WO97/18454   5/1997   (WO) .

OTHER PUBLICATIONS

Widell et al., J. of Medical Virology 35 : 253–258 (1991).*
Cooper et al., BioTechnology 9(1): 60–65 (1990).*
Lanciotti et al., J. of Clinical Microbiology 30 (3): 545–551(1992).*
Sullivan et al., Virus Research 38 : 231–239 (1995).*
Sehgal et al., International J. of Cancer 76: 451–458 (May 1998).*
Lee et al., Science 239: 1288–1291 (1988).*
Widell et al., J. of Medical Virology 44: 272–279 (1994).*
Bej et al., Critical Reviews in Biochemistry and Molecular Biology 26(3/4): 301–334 )(1991).*
Liang, P. et al. (1993). Nucleic Acids Research, 21, 3269–3275.
W.C. Powell and L.M. Matrisian, Complex Roles of Matrix Metalloproteinases in Tumor Progression.
Fillmore, Helen L. et al. (Jun. 7–11, 1997). Abstract from An AACR Special Conference in Cancer Research Joint Conference with the Joint Section on Tumors of the AANS/CNS (Cancer of the Central Nervous System), A–15.
Fillmore, Helen L. et al. (Oct. 6–9, 1996). Abstract from Differential Display and Related Techniques for Gene Discovery.
Liang, P. et al. (1992). Science, 257, 967–971.

* cited by examiner

*Primary Examiner*—Ethan Whisenant
(74) *Attorney, Agent, or Firm*—Millen White Zelano & Branigan

(57) ABSTRACT

A method of sequential consensus region-directed amplification comprising, (a) amplifying a first segment of at least one target DNA in a DNA mixture, using a first and second oligonucleotide primer, each of which hybridizes to the target DNA, and a nucleic acid polymerase, under conditions in which DNA amplification is achieved, resulting in a first segment of double-stranded DNA; (b) amplifying a second segment of the first segment of double-stranded DNA, using a third and fourth oligonucleotide primer, each of which hybridizes to the first DNA segment, and a nucleic acid polymerase, under conditions in which DNA amplification is achieved, resulting in a second segment of double-stranded DNA.

34 Claims, 3 Drawing Sheets

FIGURE 1A

| CSR | ZBR | PLR |

FIGURE 1B

Total RNA

_____ AAAA
_____ AAAAAAAA

+ oligo-dT primers T(12)VN

+ reverse transcriptase

= cDNAs with 3' T(12)VA
cDNAs with 3' T(12)VG
cDNAs with 3' T(12)VC
cDNAs with 3' T(12)VT

```
(CSR) _____ AVAAAAAAAAAAAA
(CSR) _____ TVTTTTTTTTTTTTT (CSR) _____ GVAAAAAAAAAAAA
(CSR) _____ CVTTTTTTTTTTTTT (CSR) _____ CVAAAAAAAAAAAA
(CSR) _____ GVTTTTTTTTTTTTT (CSR) _____ TVAAAAAAAAAAAA
(CSR) _____ AVTTTTTTTTTTTTT
```

```
(ZRB) _____ AVAAAAAAAAAAAAA
(ZRB) _____ TVTTTTTTTTTTTTTT
```

```
(PLR) _____ AVAAAAAAAAAA
(PLR) _____ TVTTTTTTTTTTT
```

SEQUENTIAL CONSENSUS REGION-DIRECTED AMPLIFICATION OF KNOWN AND NOVEL MEMBERS OF GENE FAMILIES

This application claims priority of provisional application Ser. No. 60/108,152, filed Oct. 3, 1997, which was converted from non-provisional application Ser. No. 08/943,162 on Sep. 30, 1998, and which disclosure is incorporated by reference in its entirety herein.

SUMMARY OF THE INVENTION

Proteins are comprised of polypeptide domains which share amino acid sequence identity and/or homology. The same domains can be identified in a variety of different proteins and protein families, generally possessing the same or similar functions. One explanation for the existence of shared domains is evolutionary. In this theory, the occurrence of common polypeptide domains among proteins suggests that the genetic information encoding them has been spread through the genome and dispersed into many different proteins. Thus, recombination and shuffling of preexisting polypeptide domains may lead to the evolution of new proteins. See, e.g., Doolittle, *Sci. Am.*, 253(4):88–99, 1985; Gilbert, *Science,* 228: 823–824. 1985.

There are many examples in which genes coding for different proteins contain homologous domains. For example, proteins as diverse as the epidermal growth factor and the low density lipoprotein receptor share homologous polypeptide domains. See, e.g., Sudhof et al., *Science,* 228:893–895, 1985. Proteins can also share more than one common domain. Proteins targets for the signaling protein tyrosine kinases share several different polypeptides domains. For instance, p85 contains SH3, BCR, SH2 (Src Homology 2), and SH2 domains arranged linearly from 5' to 3'. GAP120, on the other hand, contains a 5' to 3' arrangement of SH2, SH3, SH2, and PH (pleckstrin homology domain). See, e.g., *Exploring Genetic Mechanisms*, Singer and Berg, 1997, especially, pages 209–237.

The fact that conserved functional polypeptide domains are widespread throughout the genomes of living organisms has led to the discovery of protein sequence motifs which can be used to define and identify such functional domains in proteins. Moreover, consensus oligonucleotides can be designed, based on these motifs, and utilized to identify known and/or novel genes for a variety of different purposes.

A novel aspect of the present invention exploits the ordinal arrangement of these functional domains in genes and gene families to identify known and/or novel genes and/or analyze their expression and/or organization in the genome. In a preferred method, a set of consensus sequence oligonucleotides (e.g., more than two), each designed to a different polypeptide domain within a protein, are used to select, and divide into subsets, segments of DNA which contain the designated domains. The DNA segments are preferably selected from a heterogenous nucleic acid pool by nucleic acid amplification techniques, such as polymerase chain reaction. Since the domains are organized consecutively in both the proteins and the DNA which encode them, any differences in the organization of the domains within the DNA will be reflected in the amplification products. Thus, the size and/or absence of the selected segments discriminates between different genes and their expression patterns. This information can be useful to assess the health and vitality of living organisms.

For instance, consider performing a method of the invention on one DNA pool containing p85 and a second DNA pool containing p85 and GAP120, utilizing consensus sequence oligonucleotides based on SH2 and SH3 functional domains. If a first step of amplification (as a way of selection) is performed using the SH2 oligonucleotides, a segment of DNA would be identified from the first and second pool, each having a different size. A sequential step of amplification, using SH2 and SH3 consensus oligonucleotides, would again result in segments of different sizes, providing further information about the content of the DNA pools. The extraction of such information is useful, for example, to diagnose cancer and other cell cycle diseases.

As discussed above, in a first step of a preferred method according to the present invention, a first segment of nucleic acid is selected from a sample nucleic acid containing a mixture of different nucleic acid sequences. An example of a nucleic acid sample can be a cDNA pool or library which is prepared from a desired source, such as normal tissue, a tumor, or a part of the body in which a diffuse malignancy exists. Since cells exhibit a complex pattern of gene expression, they typically possess a heterogenous pool of mRNAs which, when transcribed into cDNA, results in an assortment of different sequences. The total cDNA mixture can be referred to as a sample DNA.

To characterize the sample, a subset of nucleic acids is selected on the basis of nucleotide sequences present in the subset but, either absent or less frequently represented, in other members of the sample. The nucleotide sequences utilized to perform the selection step are preferably consensus sequences designed on the basis of functional polypeptide domains or protein motifs. Preferably, the selection step is accomplished by nucleic acid amplification, e.g., using the polymerase chain reaction. For example, a pair of oligonucleotides primers can be chosen which contain functional domains present in a subset(s) of DNAs (see, e.g., FIG. 1A, containing domains CSR, ZBR, and PLR) whose selection is desired, but, absent in other DNAs. The DNA subset(s), whose selection is desired, can be referred to as the "target DNA." A target DNA can be comprised of one or more functional domains which share varying amounts of similarity, e.g., 100% sequence identity or less than 100% identity (i.e., sequence homology). Consequently, the oligonucleotide primers can comprise a variety of sequence types, including: sequences which are perfectly complementary to a selected domain; degenerate sequences; sequences which are less than perfectly complementary to a selected domain; consensus sequences for a desired domain or region shared by two or more nucleic acids; or even arbitrary or random sequences.

A reaction is performed on the sample nucleic acid under conditions in which amplification is achieved. Such conditions include, e.g., effective concentrations of oligonucleotides, of nucleic acid polymerase, of salt and cofactors, temperatures to achieve hybridization, etc. These conditions can be selected routinely or performed according to the conventional protocols known in the art. See, e.g., *PCR Protocols: A Guide to Methods and Applications*, Innis et al., eds., Academic Press, New York, 1990.

The result of the amplification is the production of a first segment of double-stranded nucleic acid. The segment is defined at its 5' and 3' ends by the oligonucleotide pairs utilized in the amplification reaction. By the term "segment," it is meant, e.g., a portion, part, or component of the target nucleic acid, i.e., less than the whole target nucleic acid. Thus, amplification with the oligonucleotide pair results in the production of a fragment of the target nucleic acid comprising only a part of an entire nucleotide sequence. In FIG. 1C, for instance, a degenerate 5' CSR primer is used with an oligo-dT primer in a polymerase chain reaction to produce a set of DNA segments defined at their 5' end by the CSR domain and their 3' end by oligo-dT. Since multiple different genes exist which possess the CSR domain, the reaction (e.g., when separated on a gel or by other means) will result in a ladder of differently sized DNA segments. In a preferred aspect of the invention, the first segment of nucleic acid is present in more than one type of nucleic acid, e.g., the segment is present in at least two cDNA types, each of which codes for a different but related polypeptide. The polypeptides can be members of the same and/or different class of proteins.

In certain aspects of the present invention, for instance, when expression patterns of two different tissue types are being compared (e.g., for diagnostic and treatment purposes), the first segment of double-stranded DNA may be present in one sample tissue type, but not in another. This result can be readily observed by separating the segment on the basis of size, e.g., by gel electrophoresis or on a sizing column. Alternatively, one or more segments can be present in both samples, but at different sizes or in different amounts. The abundance of the segment can be quantitated according to convention methods. For example, RT-PCR can be utilized after a particular segment has been identified and isolated.

In a preferred aspect of the invention, the first segment is subjected to a second step of amplification. In this case, the first segment can be sorted into subsets, again on the basis of nucleotide sequences which are present in some members, but arranged differently or absent in others, e.g., some members will have particular domains which are at different positions within the DNA (e.g., compare p85 and GAP120) or lacking in other members. The first segment of nucleic acid, produced by the first step of amplification, can therefore be a heterogeneous mixture, containing more than one type of nucleic acid (e.g., more than one cDNA type). To achieve this second step of sorting, a second pair of oligo-nucleotides primers are selected which contain sequences capable of hybridizing to a subset of nucleic acids within the first segment mixture. Amplification with the second pair of oligonucleotides (e.g., a third and fourth oligonucleotide) results in the production of a second segment of double-stranded nucleic acid. In FIG. 1D, for example, a degenerate 5' ZRB primer is used with an oligo-dT primer in a polymerase chain reaction to produce a second set of DNA segments defined at their 5' end by the ZBR domain and their 3' end by oligo-dT.

Many different combinations of consensus sequence primers are possible in the present invention. In Example 1, a method of the present invention is illustrated using degenerate 5' consensus primers. However, the consensus primers can be used as 3' primers, as well. FIGS. 1F and 1G show alternative schemes. For example, a second step of amplification (subsequent to FIG. 1C) can be achieved using: a 5° CSR primer in combination with a 3' ZBR primer (FIG. 1F); a 5' ZBR primer in combination with a 3' PLR primer.

The results of using different combinations of primers can differ, depending upon the nucleic acid(s) which is being analyzed. For example, after a second step of amplification (FIGS. 1D, 1F, or 1G), a second segment product can be present in some members of the first segment but missing from others. However, the differences can also be quantitative. The second segment can also be present in all members of the first segment, e.g., if the first and second domains were unique to that particular target gene.

The conditions to achieve amplification of a second segment of nucleic acid are similar to those used for the first segment with routine manipulations and adjustments, e.g., to account for the differences in sequence content of the second pair of oligonucleotides.

The amplification steps can be repeated as many times as desired to achieve further sorting of the mixture into various subsets. The method therefore works analogously to a set of graded mesh screens or sieves used to separate a mixture of particle sizes into individual sizes. Thus, an aspect of the present invention involves cataloging complex mixtures of nucleic acids on the basis of functional domains and sequence homologies.

The sequential steps of amplification can be performed without purification of the amplification product. For instance, a small portion (e.g., 2 µl of 20 µl) of the amplification reaction (e.g., from FIG. 1C) can be combined with a ZBR primer, etc, and then brought to a desired volume for a second step of amplification (e.g., FIG. 1B). The nucleic acid reaction products can also be depleted of various components (such as salt, nucleotides, oligonucleotide primers, etc.) and/or purified according to conventional methods, e.g., using spin columns or gels.

A sample nucleic acid subjected to a method of the invention can comprise any desired nucleic acid, including, e.g., cDNA, genomic DNA, RNA, polyadenylated RNA, unprocessed RNA, such as RNA before it is spliced by the cell. In general, a sample nucleic acid can be obtained from any chosen cell-type, stage of development (cell, tissue, organism, or whole organism), genotype, or pheno-type. In a preferred embodiment the nucleic is a cDNA pool prepared from a desired source. See, e.g., FIG. 1B. For example, cDNA can be prepared from: a normal tissue isolated from a living organism (at any stage of development or aging), tissue culture cells or other in vitro cultures, diseased or pathogenic cells or tissues (e.g., cancers and tumors), transgenic animals or plants, or other in vivo systems, etc. A cDNA pool or mixture can be prepared from a sample of tissue obtained from a patient who is known or suspected of having a particular disease, syndrome, or dysfunction.

A cDNA mixture can be synthesized according to various methods known to the skilled worker, e.g., Gubler and Hoffman, *Gene,* 25: 263–269, 1983. A CDNA mixture can also be prepared from mRNA using anchored oligo-dT primers (see, e.g., FIG. 1b) or degenerate oligo-dT primers in combination with a desired consensus primers, employing a reverse transcriptase. See, e.g., Liang et al., *Nucl. Acid. Res.,* 21:3269–3275, 1993; U.S. Pat. No. 5,599,672; WO97/18454. In accordance with the present invention, a primer used to synthesize the cDNA can be a consensus primer as described below, e.g., offering the advantages of RNA/DNA hybridization. In one aspect of the invention, a first step involves the synthesis of a cDNA pool as in FIG. 1B. By using oligo-dT primers having partially defined ends, this particular example shown in FIG. 1B provides a first sorting step; however, whether a sorting step is accomplished, and/or the type of sorting step which is utilized, can be routinely determined. cDNA libraries can also be employed, e.g., commercially available libraries.

A nucleic acid subjected to a method of the present invention can also be genomic nucleic acid, e.g., viral RNA or DNA, chromosomal DNA, plasmid DNA, transposable element DNA, or other such materials, obtained from various sources.

By the term "oligonucleotide primer," it is meant, e.g., a sequence of nucleotides which is effective in initiating the synthesis of a nucleic acid Generally, a primer comprises a sequence of DNA or RNA that can pair with one strand of nucleic acid and provide a free 3'-OH end at which a polymerase or reverse transcriptase initiates the synthesis of a polynucleotide strand complementary to a desired template. For the present invention, an oligonucleotide primer is less the entire gene sequence. The size of the primer can vary in size, e.g., depending upon the desired purpose. Preferred sizes include, e.g., 8–100, preferably, 10–50, 10–30 or 12–25, 10–25, 10–22, 22, etc. See, e.g., Sambrook et al., *Molecular Cloning*.

In a preferred embodiment of the invention, the oligonucleotides utilized to select the target nucleic acid contain a consensus sequence. A consensus sequence is, e.g., an idealized nucleotide sequence that represents the bases most often present at each position of two or more nucleotide sequences which have been compared to each other. A consensus sequence can be derived from sequences which have, e.g., shared functional or structural purposes. It can be defined by aligning as many known examples of a particular structural or functional domains as possible to maximize the homology. A sequence is generally accepted as a consensus when each particular base is reasonably predominant at its position, and most of the sequences which form the basis of the comparison are related to the consensus by rather few substitutions, e.g., 1–4.

The sequences upon which the consensus is based can be selected from domains of genes which have, e.g., similar or the same functional purpose. A domain which has a structural purpose is also referred to as a functional domain. Such genes can be obtained from the same or different species, and across various kingdoms, including animal, plant, prokaryote, eukaryote, archeabacteria, viruses, etc.

The consensus primers are generally designed to amplify a region of nucleic acid that contains a desired structural or functional domain. These domains can have any desired activity or function, including, activities and/or domains for: DNA synthesis (promoter), signalling, transmembrane transport, protein or nucleic acid targeting, kinase, phosphorylation, nucleic acid binding, oncogenes (for many examples, see, Singer and Berg, *Exploring Genetic Mechanisms*, 1997, which is incorporated by reference) cysteine switch, zinc binding, pexin-like, GTP binding, immunoglobulin superfamily, p53, transcription factors, growth factors, STATS, cytokines, HSP, hox, homeobox, bromeodomain, homocystinuria domain (Bateman, TIBS, 12–13, Jan. 1997), MMP domains (see, e.g., various sequences disclosed below by GenBank accession number), PAS domains (Zhulin et al., TIBS, 22:331–333, 1997), CARD domains (TIBS, 22:155, 1997), proteolytic cleavage sites (e.g., for caspases during apoptosis), SH2, SH3, domains found in receptor families, such as NMDA, serotonin, adrenergic, dopamine, leptin, growth factor, etc. A functional domain can also be any polypeptide or nucleic acid motif present in more than one protein, whether or not its function is known, and whether or not it has a function (i.e., a motif is identified but it has no apparent function).

A consensus oligonucleotide sequence, as mentioned above, can have any desired sequence, such as a complete complementary sequence to a consensus domain with no degenerate positions, or, it can include degenerate primers which comprise a mixture of oligonucleotides so that any one of several nucleotides is incorporated into an oligonucleotide at selected positions. See, e.g., Table 1 and Table 2. A consensus degenerate primer is sufficiently complementary to all types of a desired functional or structural domain, so that it is effective to amplify a nucleic acid sequence of any such domain in a target sample. Thus, a degenerate mixture of oligonucleotides can contain all possible sequences which can code for a chosen domain. The phrase "an oligonucleotide primer", "a first oligonucleotide primer", etc., means, e.g., one or more oligonucleotide sequences designed to the same consensus domain. In Table 1, CSR-1 is referred to as an oligonucleotide primer. Since it contains at least two degenerate positions, a CSR-1 primer includes eight different oligonucleotides.

A consensus primer can also be a single oligonucleotide where the degenerate regions are replaced by a "neutral" base which pairs adequately with all four conventional bases. Using a neutral base, reduces the adverse effect of mismatching because base pairs between the neutral base and its partner do not stabilize or destabilize the hybrid. Thus, to reduce degeneracy in a mixture of oligonucleotide primers, it may be desired to introduce such a neutral base, e.g., inosine.

The design of a consensus oligonucleotide primer can be accomplished by any suitable method available to the skilled worker. See, e.g., Chapter 11 in *Molecular Cloning*, Sambrook et al., 1989, for a discussion on designing oligonucleotide probes. They can be designed manually by inspecting functional domains which share sequence homology (e.g., at the amino acid or nucleic level). Codon usage can be taken into account when designing the oligonucleotides. If desired, the oligonucleotides can be tested empirically in test reaction to determine routinely whether it is useful in a method of the claimed invention. Automatic design of oligonucleotide primers can also be used, either alone or in combination with manual inspection. For instance, the manually designed sequences can be used in a primer selection program to eliminate primers less likely to work in the reactions. In addition, many computer-based algorithms are available which identify and delineate consensus elements, e.g., CoreSearch, ConsInspector, Consensus, etc. Methods for the identification of consensus elements are described, e.g., in Wolfertstetter et al., *Comp. Appl. Biosci.*, 12:71–80, 1996; Frech et al., *Nucl. Acid. Res.*, 21: 1655–1664, 1993; Frech et al., *Comp. Appl. Biosci.*, 13:109–110, 1997; Stormo and Hartzell, *Proc. Natl. Acad. Sci.*, 86:1183–1187, 1989; Hertz et al., *CABIOS*, 6:81–92, 1990. These methods and programs can be used to routinely identify consensusus sequences from nucleotide sequences which are known to possess common or related functions. Consensus elements can also be derived from nucleotide sequences having no known function or relation to each other. In addition, as mentioned, consensus sequences which are already known and available to the skilled worker can be used in the present invention. In some instances, only the amino acid sequences of a desired domain will be known. In these cases, a consensus sequence based on amino acids only can be derived and then converted into a nucleotide sequence using the known genetic code and codon usage rules. See, e.g., Jaye et al., *Science*, 233:541, 1986.

The sequence of the oligonucleotide primers used in the present invention can vary widely. Some guidelines to the selection of primer sequences are found, e.g., in Innis and Gelfand, pages 3–12, PCR Protocols: *A Guide to Methods and Applications* (Innis et al., eds., Academic Press, New York, 1990). The selection of the primers can be determined empirically, e.g., using various experimental conditions to routinely select a primer(s) and conditions which are effective for the desired purpose. Automated primer design programs are also available to the skilled worker for selection of optimal primers for the use in methods according to the present invention, e.g., Primer Premier 4 Pro and Primer Premier 4 Lite.

An oligonucleotide can be prepared using any suitable method, such as conventional phosphotriester and phosphodiester methods or automated embodiments thereof. In one such automated procedure, diethylphosphoramidites are used as starting materials and can be synthesized as described by Beaucage et al., *Tetrahedron Letters*, 22:1859–1862, 1981. A method describing synthesizing oligonucleotides on a solid support is also described in U.S. Pat. No. 4,458,066. Oligonucleotides can comprise conventional nucleotide bases, e.g., adenosine, cytosine, thymine, and guanine, but also other nucleotides, including, inosine, uracil, etc. The oligonucleotides can be modified and/or include modified nucleotides. In addition, the oligonucleotides can be labeled, e.g., at the 3' and/or 5' ends, as desired. Various modifications can be made to the primers and synthesized segments, such as attaching detectable markers (avidin, biotin, radio-active species), moieties which improve hybridization, detection, stability, etc.

In a preferred embodiment, the amplification is performed by polymerase chain reaction ("PCR"); however, other methods can be utilized, as well. PCR can be carried out according to any method available to the skilled worker. For example, PCR is described in Saiki et al., 1988, Science, 241:53; U.S. Pat. No. 4,683,202; PCR Protocols: *A Guide to Methods and Applications*, M. A. Innis et al., eds., Academic Press, 1990; PCR, Newton, C. R., 2nd ed., Springer, 1997; PCR: *Essential Techniques*, John Wiley & Sons, 1996; PCR *Cloning Protocols*, ed. Bruce A. White, Humana Press, 1997. Especially for methods of the invention involving the polymerase chain reaction, the oligonucleotides in a given pair typically have different sequences, are complementary to sequences which reside on opposite strands of the template nucleic acid, and flank the nucleic acid segment of interest which is to be amplified. PCR using a mixture of oligonucleotides based on a consensus sequence can be carried, e.g., analogously to U.S. Pat. No. 5,437,975 or Leytus et al., *Biochemistry*, 27: 1067–1074, 1988. The amplification and other reactions in accordance with the present invention can be accomplished in liquid or solid phases. For example, the oligonucleotides can be attached to solid supports, e.g., nitrocellulose, nylon, agarose, diazotized cellulose, latex solid microspheres, magnetic beads, polyacrylamides, etc., according to a desired method. See, e.g., U.S. Pat. Nos. 5,470,967, 5,476,925, 5,478,893.

An aspect of the present invention involves contacting a target nucleic acid with an oligonucleotide primer under conditions effective to achieve hybridization between the target and oligonucleotide. Hybridization conditions can be selected to achieve a binding between each nucleotide of the primer and its target. However, conditions can also be selected where mismatches exist between the primer and target. The selection of such conditions are described, e.g., in Sambrook et al., *Molecular Cloning*, Chapter 11.

As mentioned, a nucleic acid (e.g., an oligonucleotide) can be labeled according to any desired method. A nucleic acid can be labeled using radioactive tracers such as $^{32}P$, $^{35}S$, $^{125}I$, $^{3}H$, or $^{14}C$, to mention only some of the most commonly used tracers. The radioactive labeling can be carried out according to any suitable method such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of luminous or other energy at a desired wavelength, etc.

A nucleic acid polymerase means, e.g., an agent which will function to accomplish the synthesis of a nucleic acid from a nucleic acid template, generally using a suitable primer. For example, in accordance with the present invention, a segment of a target DNA is amplified using a pair of oligonucleotides which hybridize to the target DNA. A nucleic acid polymerase is utilized to achieve amplification. The polymerase can be, e.g., *E. coli* DNA polymerase I, Klenow fragment of *E. coli* DNA polymerase, Tth DNA polymerase (e.g., U.S. Pat. No. 5,192,674), ΔTth DNA polymerase, T4 DNA polymerase, Taq DNA polymerase, Klen-Taq-1 DNA polymerase, polymerase muteins (including heat-stable polymerases), reverse transcriptase, ribozyme polymerases, etc.

An aspect of the present invention relates to a method of differentiating between samples of nucleic acid in a highly specific manner. In a preferred aspect, at least two samples containing nucleic acid are distinguished on the basis of differential gene expression. For example, matrix metalloproteinases ("MMP") comprise a multigene family involved in both normal and abnormal cellular processes. See, e.g., Powell and Matrisian, *Current Topics in Microbiology*, 213 (1):1–21, 1996. MMPs are proteinases which degrade matrix molecules surrounding cells and vessels, thereby aiding in the process of cell invasion. There are at least thirteen members of the MMP family which have been cloned. Expression of several of these MMP-types are known to correlate with invasiveness. For example, it is believed that MMPs are involved in the migration of astrocytoma and glioblastoma multiforme (GBM) tumors cells from the tumor core into surrounding normal tissue in the brain. Although the MMPs differ in their substrate specificity, they possess common functional domains, including: a pre-pro region, a cysteine switch region (CSR); a zinc binding region (ZBR); a hemepexin-like or pexin-like region (PLR); a catalytic domain (CATR) which contains ZBR; and a transmembrane domain (TMD). The present invention enables the identification of MMP genes in a tumor and surrounding tissue, providing important information about the status of the disease and the target (e.g., MMP) for treating it.

The combinatorial use of consensus primers can also be applied to distinguishing expression patterns of normal tissues at different stages of development. The present method can also be applied to genomic DNA, e.g., to study gene clusters and operons or to examine the differential ordinal arrangement of genes in different species or kingdoms. For example, β-globin genes are organized in clusters. In the rabbit, four β-like genes are found in the genomic DNA: two embryonic, one pseudo, and one adult, arranged linearly in the genomic DNA. See, e.g., Lewin, *Genes III*, 1987, page 401. To study the conservation of the β-gene cluster in various species, a pair of consensus sequence primers matching the 5' first embryonic gene and the 3' last adult gene are designed and used to select a first segment of double-stranded DNA from genomic DNA using the method described above. The first segment can be subjected to a second step, e.g., using consensus sequence primers to the second embryonic gene and pseudogene which are sandwiched between the first embryonic and adult genes. In the rabbit, a first and second segment, having defined lengths are obtained. However, when genomic DNA of different species is subjected to the first and second sorting steps, the products can differ in the size of the first and/or second segment, and in the presence or absence of the first and/or second segment. This method can be applied to any desired gene cluster, including homeobox genes, collagens, integrins, hox, etc.

In another aspect of the invention, the method can be applied to the analysis of genomic DNA. Using consensus sequence oligonucleotides as described above, various characteristics of genomic DNA (in different species, different individuals of the same species, etc) can be analyzed, e.g., deletions, insertions (viruses, such as HIV, transposable elements, etc.), mutations, including repeats, intron/exon structure, etc.

Another aspect of the invention relates to kits comprising oligonucleotides and reagents for performing the claimed method, e.g., reverse transcriptase or other enzymes for synthesing cDNA from MRNA, a DNA polymerase for performing DNA amplification, buffers, etc. A kit can comprise a set of different oligonucleotides for selection of subsets from a nucleic acid mixture, e.g., mRNA or cDNA, e.g., consensus oligonucleotides comprising SPR, CSR, ZBR, CATR, PLR and/or TMR (transmembrane region) regions of a gene. These oligonucleotides have the sequences shown in Table 1 or Table 2, or they can have the reverse complementary sequences, depending upon which strand is to be copied and amplified. For example, a reverse complementary oligonucleotide of CSR-1 is 5' GGG CAC NCC RCA GCG 3' (SEQ ID NO:1). The disclosure of every sequence in this application, including sequences incorporated by reference, means both the sense and antisense sequences, e.g., for the design of consensus oligonucleotides.

Oligonucleotides of the present invention include those listed in Tables 1 and 2, the antisense of such oligonucleotides, and longer oligonucleotides which comprises the sequences, or antisense thereof, listed in Tables 1 and 2. The present invention also relates to other nucleotide sequences which can be used as consensus oligonucleotide primers in the present invention to select, amplify, and/or identify known or novel MMP, MMP-like genes, and genes containing domains therein, including sequences listed in the NCBI Entrez GenBank database by accession nos. AF007878; X90925; U38322; U38321; U38320; U37791; Y12617; Z11887; Y08622; L20471; D50477; X92521; X89576; U78045; D26512; U51914; N89507; N87076; J05556; U41078; Z48482; Z48481; X83535; X75308; HUMMATRY0; L22525; J03209. In addition: AB006421; AA497317; AB000719; U54984; U77588; D63579; X91785; AA174765; U70919; U65656; U54825; U6853; U66463; X92520; U62529; U41824; L37295; L24374; U22380; L38480; U24441; L31883; L31884; L49412; U30822; X54724; X71466; X83537; X83536; X78324; L36050; Z27093; M25663; D26514; U07775; S67830; X62622; M82858; L27424; M25664. All of such sequences are incorporated by reference, e.g., by the accession number in GenBank, or any other way in which the sequences are available. The oligonucleotides primers usefuil in the present invention can be perfectly complementary or degenerate to any of the above-mentioned sequences, especially to polypeptide and/or nucleotide domains. The primers can also be consensus primers, e.g., of the type illustrated in Tables 1 and 2. As described throughout this application, the design of consensus primers (when not already known) is routine and can be accomplished by any available method, including the automatic/ and/or manual described herein.

DRAWINGS

FIG. 1A. is schematic drawing of an MMP DNA showing the ordinal arrangement functional domains. CSR represents the cysteine-switch domain; ZBR represents the zinc binding region domain; and PLR represents the pexin-like domain.

FIG. 1B represents the production of a cDNA pool starting with RNA from a desired source. N is A, G, C, or T; V is A, G, or C.

EXAMPLE

Most, if not all, MMPs share functional domains which include a cysteine switch region, a catalytic domain, a Zn++ binding region, and a pexin-like region (FIG. 1A). Novel degenerate oligonucleotides were designed to bind specific homologous regions of MMP family members and were used in a specific combination to generate MMP-like or known MMP cDNAs and DNA segments from tissues. The degenerate oligonucleotides are all 5' primers. CSR is a degenerate oligonucleotide designed to bind the cysteine switch region. ZBR is a degenerate oligonucleotide designed to bind the Zn++ binding region and PLR is a degenerate designed to bind the pexin-like region. Various sequences are listed in Table 1 and Table 2. By the term "isolated", it meant, e.g., a form other than how it could occur in nature, e.g., in a buffer, in a dry form awaiting reconstitution, as part of a kit, etc.

Figures 1C, 1D, 1E, 1F:
FIG. 1C shows a PCR product using a degenerate CSR primer and an oligo-dT primer.
FIGS. 1D and 1E show a second and third step of amplification, employing degenerate ZRB and PLR oligonucleotide primers, respectively.
FIGS. 1F and 1G show alternative amplification schemes, using 3' consensus oligonucleotides as primers.
Figure 1G:

Degenerate primers to different consensus regions of the MMP family were designed and used with anchored oligo-dTs to screen for brain/tumor specific MMPs. Surgical sample were obtained at craniotomy for tumor resection, snap frozen, and stored at −70° C. In addition to samples from the tumor core, samples of adjacent "normal" brain that also required removal were obtained. RNA was then isolated using a commercial kit (Stratagene) and an anchored oligo-dT kit (Genosys) was used to reverse transcribe poly A+ mRNA and PCR was performed to screen for differentially expressed genes. See FIG. 1B. For conditions, see, Liang et al., *Nucl. Acid. Res.*, 21:3269–3275, 1993. Once the mRNA is reverse transcribed, the degenerate 5' primer, CSR, is used with corresponding oligo-dT primers in a polymerase chain reaction (PCR) amplification of the cDNA. FIG. 1C. The total volume is about 20 µl. From this pool of cDNA, a second step of amplification is formed using the degenerate 5' primer, ZBR, and the corresponding oligoAT 3' primers. See FIG. 1D. About 2 µl of the reaction production from the first step was used in this second step and brought up to a final volume of 20 µl. The result amplification product from the second step was subjected a third step of amplification, using the degenerate 5' primer, PLR, under conditions, etc., as described above.

The pools of cDNA were then separated on 4% sequencing gels and differentially expressed genes (represented by bands due to the incorporation of $^{32}P$ used in the final step of PCR), were then isolated, reamplified, and sequenced.

From the foregoing description, one skilled in the art can easily ascertain the essential characteristics of this invention, and without departing from the spirit and scope thereof, can make various changes and modifications of the invention to adapt it to various usages and conditions.

For other aspects of the nucleic acids, etc., reference is made to standard textbooks of molecular biology and protein science. See, e.g., Davis et al. (1986), *Basic Methods in Molecular Biology,* Elsevir Sciences Publishing, Inc., New York; Hames et al. (1985), *Nucleic Acid Hybridization,* IL Press, *Molecular Cloning,* Sambrook et al.; *Current Protocols in Molecular Biology,* Edited by F. M. Ausubel et al., John Wiley & Sons, Inc; *Current Protocols in Hunan Genetics,* Edited by Nicholas C. Dracopoli et al., John Wiley & Sons, Inc.; *Current Protocols in Protein Science*; Edited by John E. Coligan et al., John Wiley & Sons, Inc.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

TABLE 1

| SEQ ID | | consensus sequence |
|---|---|---|
| *cysteine switch region (CSR)* | | |
| (SEQ ID NO:2) | CSR-1 | 5'CGC TGY GGN GTG CCC 3' |
| (SEQ ID NO:3) | CSR-2 | 5'ATG MGN AAR CCN CGC TGT 3' |
| (SEQ ID NO:4) | CSR-3 | 5'MTS MRV MMN CCC CGC TGT 3' |
| (SEQ ID NO:5) | CSR-4 | 5'GTN CCN GAY GTG 3' |
| *zinc binding region (ZBR)* | | |
| (SEQ ID NO:6) | ZBR-1 | 5'TTC YTG NGC TGC C 3' |
| (SEQ ID NO:7) | ZBR-2 | 5'SAC TTC TYG NGC TGC C 3' |
| (SEQ ID NO:8) | ZBR-3 | 5'TTC RTC NGC TGC 3' |
| (SEQ ID NO:9) | ZBR-4 | 5'TTC RTC NGC TGC 3' |
| (SEQ ID NO:10) | ZBR-5 | 5'GCN GCN CAY GAA 3' |
| *catalytic dornain (CATR)* | | |
| (SEQ ID NO:11) | CATR-1 | 5'GCN GAY ATN ATG 3' |
| *hemepexin-like region (PLR)* | | |
| (SEQ ID NO:12) | PLR-1 | 5'CTN CCN AGY CCT 3' |

N = (A,C,G,T) M = (A,C) R = (A,G) S = (C,G) Y = (C,T)

TABLE 2

Signal peptide region (SPR)

5'-3'

| ctgctgctgctgctc | (SEQ ID NO:13) |
|---|---|
| ctgctgctyctgctc | (SEQ ID NO:14) |
| ctgctgtgygtngcn | (SEQ ID NO:15) |
| ctgctgtgy | (SEQ ID NO:16) |

TABLE 2-continued

| ctgctgtgygtngc | (SEQ ID NO:17) |
|---|---|
| ctgctgctgtgy | (SEQ ID NO:18) |

Propeptide region (PPR)

5'-3'

| aaggaygtnaag | (SEQ ID NO:19) |
|---|---|
| aargaygtnaar | (SEQ ID NO:20) |
| aaggaygtnaagcagttc | (SEQ ID NO:21) |
| aargaygtnaarcagttc | (SEQ ID NO:22) |
| aggaggaar | (SEQ ID NO:23) |
| aggaggrrngac | (SEQ ID NO:24) |
| aggaggrrngat | (SEQ ID NO:25) |
| aggaggrrgay | (SEQ ID NO:26) |

Catalytic domain CATR these in addition to CATR1 (CATR)

5'-3'

| cargaygayathgay | (SEQ ID NO:27) |
|---|---|
| cargaygayatcgat | (SEQ ID NO:28) |
| caggaygayathgay | (SEQ ID NO:29) |
| caggaygayaycgat | (SEQ ID NO:30) |
| caggatgatatcgat | (SEQ ID NO:31) |
| caggatgacatcgat | (SEQ ID NO:32) |

B = (C,G,T)   M = (A,C)       V = (A,C,G)

D = (A,G,T)   N = (A,C,G,T)   Y = (C,T)

H = (A,C,T)   R = (A,G)       W = (A,T)

K = (G,T)     S = (C,G)

What is claimed:

1. A method of sequential consensus region-directed amplification for sorting a mixture of DNAs into two or more subsets comprising,
   a) amplifying a first segment of at least one target DNA in a DNA mixture, using a first and second oligonucleotide primer, each of which hybridizes to the target DNA, and a nucleic acid polymerase, under conditions in which DNA amplification is achieved, resulting in a first segment of double-stranded DNA;
   b) amplifying a second segment of the first segment of double-stranded DNA, using third and fourth pools of oligonucleotide primers which comprise degenerate oligonucletoides, each of which pool comprises consensus sequences corresponding to functional domains and hybridizes to the first DNA segment, and a nucleic acid polymerase, under conditions in which DNA amplification is achieved, resulting in a second segment of double-stranded DNA, and
   c) identifying at least two subsets of amplified DNAs, whereby said subsets are identified based on the presence of one or more consensus regions.

2. A method of claim 1, wherein at least one oligonucleotide primer is coding for a first consensus sequence.

3. A method of claim 2, wherein the primer is a pool of oligonucleotides coding for the first consensus sequence.

4. A method of claim 1, wherein at least two oligonucleotide primers are coding for a first and second consensus sequence.

5. A method of claim 4, wherein the primers are a pool of oligonucleotides coding for the first and second consensus sequences.

6. A method of claim 1, wherein oligonucleotide primers one, two, three, and four, are each different from each other.

7. A method of claim 1, wherein the DNA is cDNA.

8. A method of claim 7, further comprising synthesizing a cDNA mixture, prior to step a), from a sample of RNA obtained from a source.

9. A method of claim 1, wherein the DNA mixture is synthesized employing a degenerate consensus oligonucleotide primer and oligo-dT.

10. A method of claim 8, wherein the source of RNA is normal, tumor or potentially diseased tissue.

11. A method of claim 8, wherein the source of RNA is a brain tumor.

12. A method of claim 1, wherein the DNA is a cDNA mixture is prepared from the RNA of a normal, tumorous or potentially diseased tissue.

13. A method of claim 1, further comprising c) amplifying a third segment of the second segment of double-stranded DNA, using a fifth and sixth oligonucleotide primer, each of which hybridizes to the second DNA, and a nucleic acid polymerase, under conditions in which DNA amplification is achieved resulting in a third segment of double-stranded DNA.

14. A method of claim 1, wherein step b) is repeated at least once, using different sets of oligonucleotides primers than employed in steps a) and b).

15. An isolated oligonucleotide consisting essentially of a primer of Table 1.

16. An isolated oligonucleotide consisting essentially of a primer of Table 2.

17. An isolated oligonucleotide consisting essentially of a primer which is fully complementary to a primer of Table 1.

18. An isolated oligonucleotide consisting essentially of a primer which is fully complementary to a primer of Table 2.

19. A kit for sequential consensus region-directed amplification comprising, an oligonucleotide consisting essentially of a primer of Table 1 or 2 and a DNA polymerase.

20. A kit of claim 19, further comprising a reverse transcriptase.

21. A kit of claim 19, wherein the oligonucleotide is an oligonucleotide which is fully complementary to a primer of Table 1 or Table 2.

22. A method of sequential consensus region-directed amplification for distinguishing gene expression patterns in two samples, comprising,
   a) converting at least two RNAs in each of the two samples to DNA, thereby generating for each sample a mixture of target DNAs;
   b) amplifying a first segment of at least two target DNAs in each DNA mixture, using a first and second oligonucleotide primer, each of which hybridizes to the target DNAs, and a nucleic acid polymerase, under conditions in which DNA amplification is achieved, resulting in a first set of segments of double-stranded DNA;
   c) amplifying a second segment of each of the first segments of double-stranded DNA, using a third and fourth oligonucleotide primer, each of which hybridizes to the first DNA segments, and a nucleic acid polymerase, under conditions in which DNA amplification is achieved, resulting in a second set of segments of double-stranded DNA; and
   d) distinguishing differences in the amounts and/or patterns of double stranded DNA segments generated in the two samples.

23. The method of claim 1, wherein the DNA mixture comprises two or more members of a matrix metalloproteinase multigene family.

24. A method of claim 22, wherein at least one oligonucleotide primer is coding for a first consensus sequence.

25. A method of claim 22, wherein the primer is a pool of oligonucleotides coding for the first consensus sequence.

26. A method of claim 22, wherein at least two oligonucleotide primers are coding for a first and second consensus sequence.

27. A method of claim 22, wherein the primers are a pool of oligonucleotides coding for the first and second consensus sequences.

28. A method of claim 22, wherein oligonucleotide primers one, two, three, and four, are each different from each other.

29. A method of claim 22, wherein the DNA mixture is synthesized employing a degenerate consensus oligonucleotide primer and oligo-dT.

30. A method of claim 22, wherein the source of RNA is normal, tumor or potentially diseased tissue.

31. A method of claim 22, wherein the source of RNA is a brain tumor.

32. A method of claim 22, wherein the DNA is a cDNA mixture is prepared from the RNA of a normal, tumorous or potentially diseased tissue.

33. A method of claim 22, further comprising e) amplifying a third segment of the second segment of double-stranded DNA, using a fifth and sixth oligonucleotide primer, each of which hybridizes to the second DNA, and a nucleic acid polymerase, under conditions in which DNA amplification is achieved resulting in a third segment of double-stranded DNA.

34. A method of claim 22, wherein step b) is repeated at least once, using different sets of oligonucleotides primers than employed in steps a) and b).

* * * * *

SEQUENCE LISTING

<160> NUMBER OF SEQ ID NOS: 32

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (7)
<223> OTHER INFORMATION: A, T, C, G, other or unknown

<400> SEQUENCE: 1
gggcacnccr cagcg                                                    15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 2
cgctgyggng tgccc                                                    15

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (6)
<223> OTHER INFORMATION: A, T, C, G, other or unknown
<220> FEATURE:
<221> NAME/KEY: MOD_RES
<222> LOCATION: (12)
<223> OTHER INFORMATION: A, T, C, G, other or unknown

<400> SEQUENCE: 3
atgmgnaarc cncgctgt                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 4
mtsmrvmmnc cccgctgt                                                 18

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (3)
<223> OTHER INFORMATION: A, T, C, G, other or unknown
<220> FEATURE:
<221> NAME/KEY: MOD_RES
<222> LOCATION: (6)
<223> OTHER INFORMATION: A, T, C, G, other or unknown

<400> SEQUENCE: 5
gtnccngayg tg                                                    12

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (7)
<223> OTHER INFORMATION: A, T, C, G, other or unknown

<400> SEQUENCE: 6
ttcytgngct gcc                                                   13

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (10)
<223> OTHER INFORMATION: A, T, C, G, other or unknown

<400> SEQUENCE: 7
sacttctygn gctgcc                                                16

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (7)
<223> OTHER INFORMATION: A, T, C, G, other or unknown

<400> SEQUENCE: 8
ttcrtcngct gc                                                    12

<210> SEQ ID NO 9

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (7)
<223> OTHER INFORMATION: A, T, C, G, other or unknown

<400> SEQUENCE: 9
ttcrtcngct gc                                                           12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (3)
<223> OTHER INFORMATION: A, T, C, G, other or unknown
<220> FEATURE:
<221> NAME/KEY: MOD_RES
<222> LOCATION: (6)
<223> OTHER INFORMATION: A, T, C, G, other or unknown

<400> SEQUENCE: 10
gcngcncayg aa                                                           12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (3)
<223> OTHER INFORMATION: A, T, C, G, other or unknown
<220> FEATURE:
<221> NAME/KEY: MOD_RES
<222> LOCATION: (9)
<223> OTHER INFORMATION: A, T, C, G, other or unknown

<400> SEQUENCE: 11
gcngayatna tg                                                           12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (3)
<223> OTHER INFORMATION: A, T, C, G, other or unknown
<220> FEATURE:
<221> NAME/KEY: MOD_RES
<222> LOCATION: (6)
<223> OTHER INFORMATION: A, T, C, G, other or unknown

<400> SEQUENCE: 12
```
ctnccnagyc ct                                                    12

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 13
ctgctgctgc tgctc                                                 15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 14
ctgctgctyc tgctc                                                 15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (12)
<223> OTHER INFORMATION: A, T, C, G, other or unknown
<220> FEATURE:
<221> NAME/KEY: MOD_RES
<222> LOCATION: (15)
<223> OTHER INFORMATION: A, T, C, G, other or unknown

<400> SEQUENCE: 15
ctgctgtgyg tngcn                                                 15

<210> SEQ ID NO 16
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 16 ctgctgtgy                                                         9

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (12)

```
<223> OTHER INFORMATION: A, T, C, G, other or unknown

<400> SEQUENCE: 17
ctgctgtgyg tngc                                                         14

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 18
ctgctgctgt gy                                                           12

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 19
aaggaygtna ag                                                           12

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 20
aargaygtna ar                                                           12

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 21
aaggaygtna agcagttc                                                     18

<210> SEQ ID NO 22
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 22
aargaygtna arcagttc                                                    18

<210> SEQ ID NO 23
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 23 aggaggaar                                                               9

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 24
aggaggrrng ac                                                          12

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 25
aggaggrrng at                                                          12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases
<220> FEATURE:
<221> NAME/KEY: MOD_RES
<222> LOCATION: (9)
<223> OTHER INFORMATION: A, T, C, G, other or unknown

<400> SEQUENCE: 26
```

```
aggaggrrng ay                                                     12

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 27
cargaygaya thgay                                                  15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 28
cargaygaya tcgat                                                  15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 29
caggaygaya thgay                                                  15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 30
caggaygaya tcgat                                                  15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide, consensus sequence from human
      matrix metalloproteinases

<400> SEQUENCE: 31
caggatgata tcgat                                                  15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
           oligonucleotide, consensus sequence from human
           matrix metalloproteinases

<400> SEQUENCE: 32
caggatgaca tcgat                                                         15
```